US00PP14635P29

(12) United States Plant Patent
Knosher

(10) Patent No.: US PP14,635 P2
(45) Date of Patent: Mar. 23, 2004

(54) GAURA PLANT NAMED 'BALTINROSE'

(50) Latin Name: *Gaura lindheimeri*
Varietal Denomination: Baltinrose

(75) Inventor: Lynne Knosher, St. Charles, IL (US)

(73) Assignee: Ball Horticultural Company, West Chicago, IL (US)

( * ) Notice: Subject to any disclaimer, the term of this patent is extended or adjusted under 35 U.S.C. 154(b) by 16 days.

(21) Appl. No.: 10/329,635

(22) Filed: Dec. 26, 2002

(51) Int. Cl.[7] ..... A01H 5/00
(52) U.S. Cl. ..... Plt./227
(58) Field of Search ..... Plt./226

*Primary Examiner*—Kent Bell
(74) *Attorney, Agent, or Firm*—Wood, Phillips, Katz, Clark & Mortimer

(57) ABSTRACT

A new and distinct Gaura plant named 'Baltinrose', characterized by its medium pink flowers, upright and slightly spreading growth habit and dark green foliage.

2 Drawing Sheets

Latin name of genus and species of plant claimed: *Gaura lindheimeri.*
Variety denomination: 'Baltinrose'.

BACKGROUND OF INVENTION

The present invention comprises a new and distinct Gaura plant, botanically known as *Gaura lindheimeri*, and hereinafter referred to by the cultivar name 'Baltinrose'.

The new cultivar was developed by the inventor in a controlled breeding program during June 1999, at Elburn, Ill. The objective of the breeding program was the development of Gaura cultivars with a well-branched, compact habit, continuous flowering and dark green foliage.

The female (seed) parent of 'Baltinrose' was a proprietary Gaura selection designated '0007-1'(non-patented, characterized by its white flowers. The male (pollen) parent of 'Baltinrose' was commercially available Gaura variety 'Siskyou Pink' (non-patented) characterized by its medium pink flowers. 'Baltinrose' was selected in August 2000 as a single flowering plant from within the progeny of the above stated cross and was initially designated '0012-B1'.

Asexual reproduction of the new cultivar at West Chicago, Ill. was carried out by the use of terminal stem cuttings has demonstrated that the new Gaura reproduces true to type with the characteristics as herein described are firmly fixed and retained through successive generations of such asexual propagation.

SUMMARY OF INVENTION

It was found that the cultivar of the present invention:

(a) exhibits medium pink colored flowers, (b) forms dark green foliage, and (c) exhibits an upright and slightly spreading growth habit.

The new cultivar of the present invention can be compared to its male parent 'Siskiyou Pink'. In side-by-side comparison, plants of the new cultivar have darker pink flowers than those of 'Siskiyou Pink'.

BRIEF DESCRIPTION OF PHOTOGRAPH

The accompanying photographs show as nearly true as it is reasonably possible to make the same in color illustrations of this type, typical flower and foliage characteristics of the new cultivar. The plants were grown in 10 cm pots for 13 weeks in a greenhouse at West Chicago, Ill.

DETAILED BOTANICAL DESCRIPTION

Figure 1:
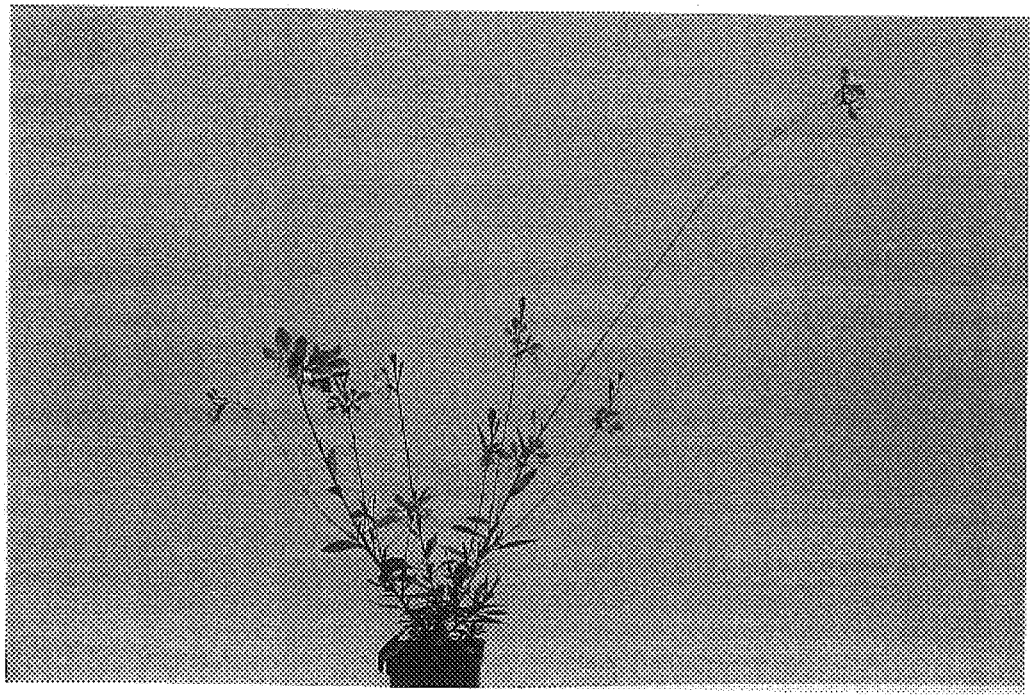
FIG. 1 illustrates the overall growth habit of the new cultivar.
Figure 2:
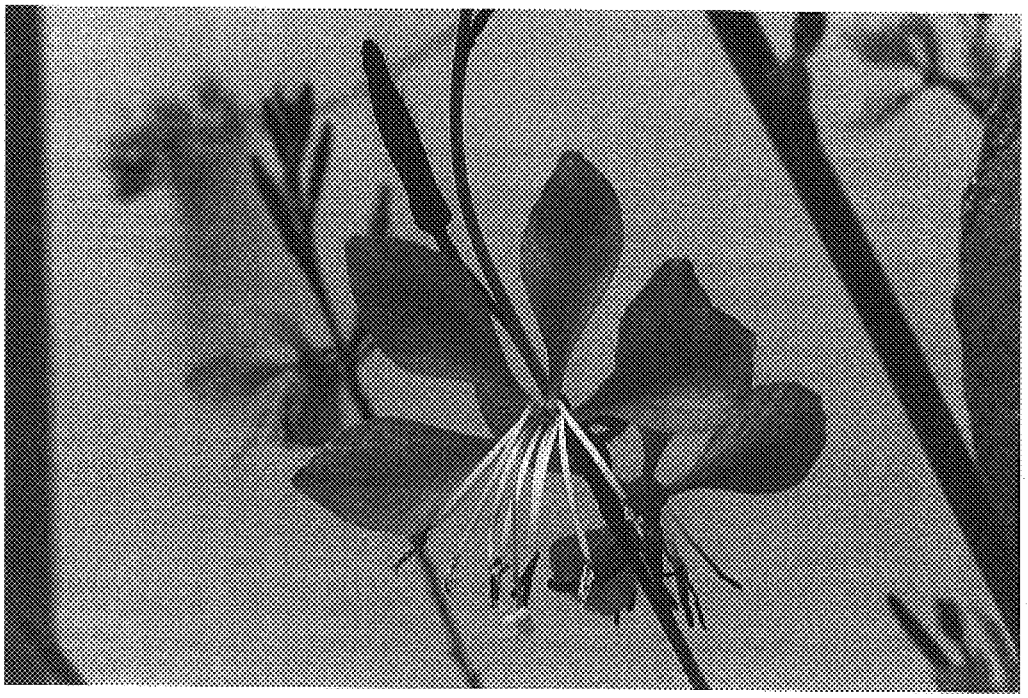
FIG. 2 illustrates a close up view of individual flowers of the new cultivar.

The new cultivar has not been observed under all possible environmental conditions to date. Accordingly, it is possible that the phenotype may vary somewhat with variations in the environment, such as temperature, light intensity, and day length. The chart used in the identification of colors described herein is The R.H.S. Colour Chart of The Royal Horticultural Society, London, England. The color values were determined on Apr. 15, 2002. The readings were taken between 1:00 and 3:00 p.m. under natural daylight conditions. The plants were produced from cuttings taken from stock plants and were grown in a double polycarbonate covered greenhouse under conditions comparable to those used in commercial practice. The plants were grown for 12 weeks while utilizing a soilless growth medium and maintaining temperatures of approximately 70° to 75° F. (21° to 24° C.) during the day and approximately 55° to 60° F. (13° to 15° C.) during the night and light levels of 5,000 to 9,000 footcandles.

Classification:
*Botanical.*—*Gaura lindheimeri* cultivar 'Baltinrose'.
Parentage:
*Female parent.*—Proprietary Gaura selection 0007-1.
*Male parent.*—Commercially available Gaura variety 'Siskyou Pink'.
Propagation:
*Type cutting.*—Terminal tip.
*Time to initiate roots.*—Approximately 14 to 21 days.
*Root description.*—Fibrous, branching.
Plant description:
*Habit of growth.*—Moderately vigorous. Pinching improves branching. The foliage of a mature plant, 12 weeks after the planting of a rooted cutting, measures approximately 22.7 cm in height and approximately 21.8 cm in width with approximately 8.4 flowering branches.

*Form.*—Upright.

*Branch.*—Length: Approximately 22.7 cm. Diameter: Approximately 3 mm. Texture: Moderate amount of short stiff hairs. Hairs become longer toward tip. Color: 138A with overlay of 185A.

*Foliage.*—Type: Simple. Arrangement: Alternate. Shape: Oblanceolate. Margin: Dentate. Apex: Acute. Base: Attenuate and sessile. Upper and lower surfaces are densely covered with short, soft hairs. Leaf length: Approximately 6 cm. Width: Approximately 1.3 cm. Upper surface of mature foliage is 137A and lower surface is 137B. Upper and lower surfaces have pinnate venation. Color of venation on both surfaces is 143C.

Inflorescence description:

*Type.*—Spicate racemes.

*Length.*—Approximately 15 cm.

*Diameter.*—Approximately 8 cm.

*Number of flowers per raceme.*—Approximately 3.

Flowering description:

*Flowering habit.*—Freely flowering.

*Natural flowering season.*—Year round in greenhouse environment and spring through autumn.

Flower description:

*Fragrance.*—Light.

*Shape.*—Round.

*Lastingness of bloom.*—Approximately 3 days.

*Pedicel.*—Length: Approximately 3 mm. Diameter: Approximately 1 mm. Aspect: At acute angle to branch. Texture: Pubescent with short, stiff hairs. Color: 176B.

*Corolla.*—Width: Approximately 3.3 cm. Length: Approximately 2.5 cm. Depth: Approximately 8 mm. Color: When fully open, the upper and lower surfaces are N66C with venation of 67C. Upper and lower surfaces of petals are smooth.

*Petals.*—Five, non-overlapping. Shape: Oblanceolate. Margin: Entire. Apex: Acute. Base: Attenuate. Length: Approximately 1.9 cm. Width: Approximately 1 cm. When fully open, the upper and lower surfaces are between N66C and N66D with venation of 67C. Upper and lower surfaces of petals are smooth.

*Bud.*—Cigar shaped. Length: Approximately 1.7 cm. Color: 59A when closed, 67B at first color. Diameter: Approximately 2.2 mm.

*Sepal.*—Quantity: 4. Lanceolate in shape. Length: Approximately 1.7 cm. Width: Approximately 1 mm. Apex: Acute. Margin: Entire. Upper surface of sepals is moderately pubescent. Lower surface has no pubescence. Upper and lower surfaces are 60B.

*Bract.*—Number per flower: Two. Shape: Lanceolate. Length: 1 cm. Diameter: 2 mm. Apex: Acuminate. Base: Truncate. Margin: Entire. Color upper and lower: 145D.

*Reproductive organs.*—There are 8 stamens. Stamen length: Approximately 8 mm. Stamen color: N66B at tip, N66D at base. The anther length: Approximately 3 mm. Anther color: 59A. Pollen amount: Moderate. Pollen color: 2B. There is one pistil, 2.6 cm in length. Stigma length: Approximately 3 mm. Stigma color: 2D. Style length: Approximately 2 cm. Style color: N66B at apex and N66C in mid portion. Ovary length: Approximately 6 mm. Ovary color: 60A.

Seed production: Seed production has not been observed.

Disease resistance: Resistance to pathogens has not been observed.

Hardiness zone: 'Baltinrose' is hardy in zones nine (9) and above.

I claim:

1. A new and distinct *Gaura lindheimeri* plant named 'Baltinrose' substantially as herein shown and described, which:

(a) exhibits medium pink flowers, (b) forms dark green foliage, and (c) exhibits an upright and slightly spreading growth habit.

* * * * *